United States Patent
Barrus et al.

(10) Patent No.: US 10,292,736 B2
(45) Date of Patent: May 21, 2019

(54) ROD REDUCTION DEVICE AND METHOD OF USE

(71) Applicant: K2M, Inc., Leesburg, VA (US)

(72) Inventors: Michael Barrus, Redondo Beach, CA (US); Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 16/021,201

(22) Filed: Jun. 28, 2018

(65) Prior Publication Data

US 2018/0303516 A1 Oct. 25, 2018

Related U.S. Application Data

(60) Continuation of application No. 15/496,768, filed on Apr. 25, 2017, now Pat. No. 10,034,689, which is a continuation of application No. 15/394,025, filed on Dec. 29, 2016, now Pat. No. 9,655,664, which is a division of application No. 14/609,868, filed on Jan.
(Continued)

(51) Int. Cl.
| | |
|---|---|
| *A61B 17/70* | (2006.01) |
| *A61B 17/88* | (2006.01) |
| *A61B 17/00* | (2006.01) |

(52) U.S. Cl.
CPC ...... *A61B 17/7001* (2013.01); *A61B 17/7086* (2013.01); *A61B 17/7089* (2013.01); *A61B 17/88* (2013.01); *A61B 17/8872* (2013.01); *A61B 17/8875* (2013.01); *A61B 2017/00407* (2013.01)

(58) Field of Classification Search
CPC ............ A61B 17/8886; A61B 17/8891; A61B 17/7086; A61B 17/8872; A61B 17/88; A61B 17/8875
See application file for complete search history.

(56) References Cited

U.S. PATENT DOCUMENTS

D346,217 S 4/1994 Sparker et al.
5,720,751 A * 2/1998 Jackson ............. A61B 17/7032
606/104
(Continued)

FOREIGN PATENT DOCUMENTS

FR 2985166 A1 7/2013
JP 2008508935 A 3/2008

OTHER PUBLICATIONS

Definition of "anvil"; accessed from www.dictionary.com on Apr. 1, 2014.
(Continued)

*Primary Examiner* — Julianna N Harvey
(74) *Attorney, Agent, or Firm* — Carter, DeLuca & Farrell LLP

(57) ABSTRACT

Provided is a novel rod reducing device including a screw jack mechanism that is moveably engaged with an elongated grasping fork assembly, the screw jack mechanism having an elongated threaded portion, the elongated threaded portion being connected at its most distal end to a rod contact member, which is positioned in sliding circumferential contact with each of the two opposing elongated grasping members and the most proximal end of the elongated threaded portion terminating in a controlling member, which can be activated in a measured and controlled manner. A method of using the device is also provided.

27 Claims, 8 Drawing Sheets

Related U.S. Application Data 30, 2015, now Pat. No. 9,532,816, which is a continuation of application No. 11/777,730, filed on Jul. 13, 2007, now Pat. No. 8,961,523.

(56) References Cited

U.S. PATENT DOCUMENTS

| | | | |
|---|---|---|---|
| 6,056,749 | A | 5/2000 | Kuslich |
| 6,123,707 | A | 9/2000 | Wagner |
| 6,183,472 | B1 | 2/2001 | Lutz |
| 6,875,211 | B2 | 4/2005 | Nichols et al. |
| 6,957,758 | B2 | 10/2005 | Aranyi |
| 7,462,182 | B2 | 12/2008 | Lim |
| 7,481,813 | B1 | 1/2009 | Purcell |
| 7,572,281 | B2 | 8/2009 | Runco et al. |
| 7,591,836 | B2 | 9/2009 | Dick et al. |
| 7,655,008 | B2 | 2/2010 | Lenke et al. |
| 7,824,413 | B2 | 11/2010 | Varieur et al. |
| 7,887,539 | B2 | 2/2011 | Dunbar, Jr. et al. |
| 7,922,749 | B2 | 4/2011 | Dewey |
| 7,927,334 | B2 | 4/2011 | Miller et al. |
| 7,988,694 | B2 | 8/2011 | Barrus et al. |
| 8,147,524 | B2 | 4/2012 | Vallespir |
| 8,152,810 | B2 | 4/2012 | Jackson |
| 8,162,991 | B2 | 4/2012 | Strauss et al. |
| 8,192,438 | B2 | 6/2012 | Garamszegi |
| 8,961,523 | B2 | 2/2015 | Barrus et al. |
| 9,532,816 | B2 | 1/2017 | Barrus et al. |
| 9,655,664 | B2 | 5/2017 | Barrus et al. |
| 2003/0004519 | A1 | 1/2003 | Torode et al. |
| 2003/0009168 | A1 | 1/2003 | Beale et al. |
| 2003/0225408 | A1 | 12/2003 | Nichols et al. |
| 2004/0147937 | A1 | 7/2004 | Dunbar et al. |
| 2004/0267275 | A1 | 12/2004 | Cournoyer et al. |
| 2005/0096653 | A1 | 5/2005 | Doubler et al. |
| 2005/0131422 | A1 | 6/2005 | Anderson et al. |
| 2005/0149053 | A1* | 7/2005 | Varieur ............ A61B 17/7086 606/104 |
| 2005/0171540 | A1 | 8/2005 | Lim et al. |
| 2005/0192570 | A1 | 9/2005 | Jackson |
| 2005/0192579 | A1 | 9/2005 | Jackson |
| 2005/0261702 | A1 | 11/2005 | Oribe et al. |
| 2006/0036255 | A1 | 2/2006 | Pond et al. |
| 2006/0069391 | A1 | 3/2006 | Jackson |
| 2006/0074418 | A1 | 4/2006 | Jackson |
| 2006/0079909 | A1* | 4/2006 | Runco ............... A61B 17/7076 606/99 |
| 2006/0089651 | A1 | 4/2006 | Trudeau et al. |
| 2006/0111713 | A1 | 5/2006 | Jackson |
| 2006/0149238 | A1 | 7/2006 | Sherman et al. |
| 2006/0195097 | A1 | 8/2006 | Evans et al. |
| 2006/0241641 | A1 | 10/2006 | Albans et al. |
| 2006/0247630 | A1 | 11/2006 | Iott et al. |
| 2006/0293692 | A1 | 12/2006 | Whipple et al. |
| 2007/0093817 | A1 | 4/2007 | Barrus et al. |
| 2007/0213714 | A1 | 9/2007 | Justis |
| 2007/0213722 | A1 | 9/2007 | Jones et al. |
| 2008/0015601 | A1 | 1/2008 | Castro et al. |
| 2008/0045955 | A1 | 2/2008 | Berrevoets et al. |
| 2011/0118791 | A1 | 5/2011 | Nunley et al. |
| 2012/0277808 | A1 | 11/2012 | May |
| 2014/0163617 | A1 | 6/2014 | Boachie-Adjei et al. |

OTHER PUBLICATIONS

International Search Report and Written Opinion corresponding to PCT/US2009/047002, completed Jul. 27, 2009 and dated Aug. 3, 2009; 7 pages.
Extended European Search Report corresponding to EP 09763592.4, completed May 8, 2013 and dated May 17, 2013; 7 pages.
Answer and Counterclaim of Defendants Orthopediatrics Corp. and Orthopediatrics US Distribution Corp. dated Mar. 6, 2017.
K2M, Inc.'s Complaint for Patent Infringement dated Jan. 20, 2017.
Declaration of Ottie Pendleton in Support of Petition for Inter Partes Review of U.S. Pat. No. 9,532,816 executed Jan. 8, 2018 for Inter Partes Case No. IPR 2018-00429.
Petition for Inter Partes Review of U.S. Pat. No. 9,532,816 dated Jan. 8, 2018 for Inter Partes Case No. IPR 2018-00429.
Declaration of Ottie Pendleton in Support of Petition for Inter Partes Review of U.S. Pat. No. 9,532,816 executed Jan. 22, 2018 for Inter Partes Case No. IPR 2018-00521.
Petition for Inter Partes Review of U.S. Pat. No. 9,532,816 dated Jan. 22, 2018 for Inter Partes Case No. IPR 2018-00521.
AcroMed Corp., ISOLA Spinal Sysytem, Ordering Information for Implants and Instruments, Mar. 1994.
K2M, Inc., Mesa Spinal System, www.K2M.com, Jun. 2006, 2 pages.
Defendant's Orthopediatrics Corp.'s and Orthopediactrics US Distribution Corp.'s Second Supplemental Invalidity Contentions.
Order Construing the Terms of U.S. Pat. No. 9,532,816 and U.S. Pat. No. 9,655,664.
Decision regarding Case No. IPR2018-00521 regarding U.S. Pat. No. 9,532,816 entered Jun. 28, 2018.
Decision regarding Case No. IPR2018-00429 regarding U.S. Pat. No. 9,532,816 entered Jun. 28, 2018.
DePuy AcroMed Corp., ISOLA Spinal System, Ordering Information for Implants and Instruments, 1999.
DePuy AcroMed, ISOLA/VSP Spine Systems, Product Catalog, 2002.
DePuy AcroMed Corp., Lumbar Degenerative Pathologies Comprehensive Low Back Set for Intraoperative Flexibility, 1998.
Declaration of Ottie Pendleton in Support of Petition for Inter Partes Review of U.S. Pat. No. 9,655,664 executed Aug. 21, 2018 for Inter Partes Case No. IPR2018-01546.
DePuy AcroMed Corporation Ordering Information for Implants and Instruments, Dec. 1998.
Petition for Inter Partes Review of U.S. Pat. No. 9,655,664 dated Aug. 21, 2018 for Inter Partes Case No. IPR2018-01546.
Declaration of Ottie Pendleton in Support of Petition for Inter Partes Review of U.S. Pat. No. 9,655,664 executed Aug. 21, 2018 for Inter Partes Case No. IPR2018-01547.
Petition for Inter Partes Review of U.S. Pat. No. 9,655,664 dated Aug. 21, 2018 for Inter Partes Case No. IPR2018-01547.
Declaration of Ottie Pendleton in Support of Petition for Inter Partes Review of U.S. Pat. No. 9,655,664 executed Aug. 21, 2018 for Inter Partes Case No. IPR2018-01548.
Petition for Inter Partes Review of U.S. Pat. No. 9,655,664 dated Aug. 21, 2018 for Inter Partes Case No. IPR2018-01548.

* cited by examiner

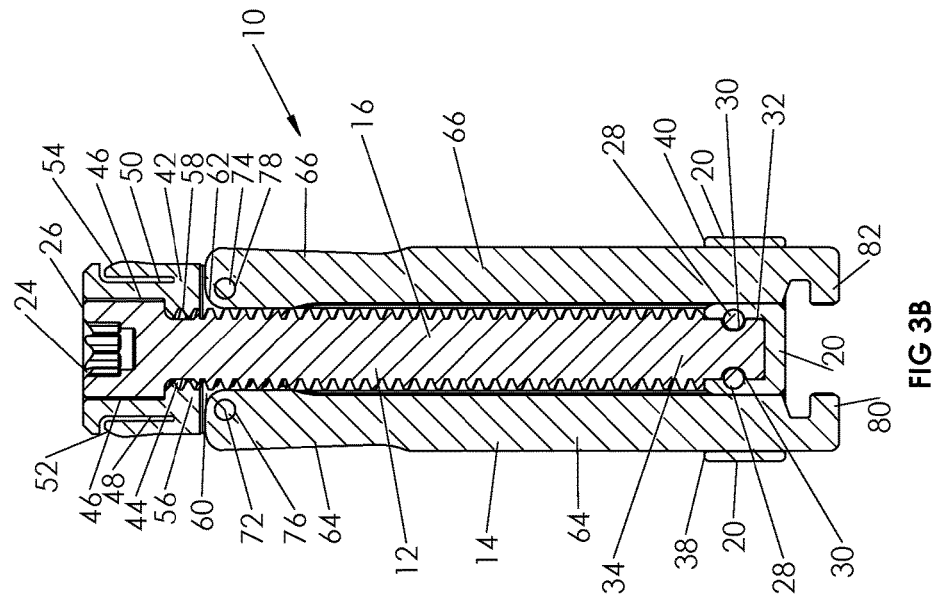
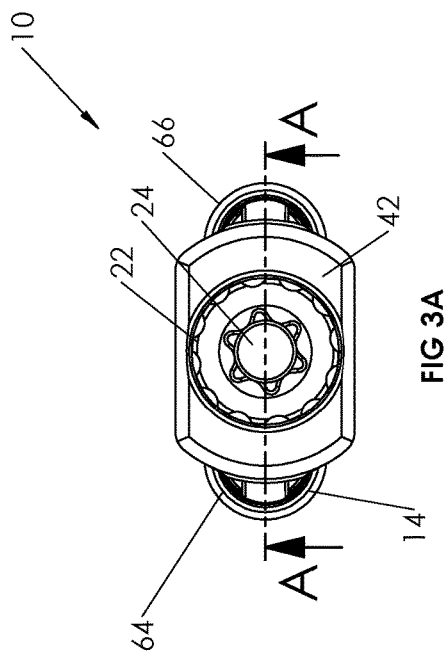

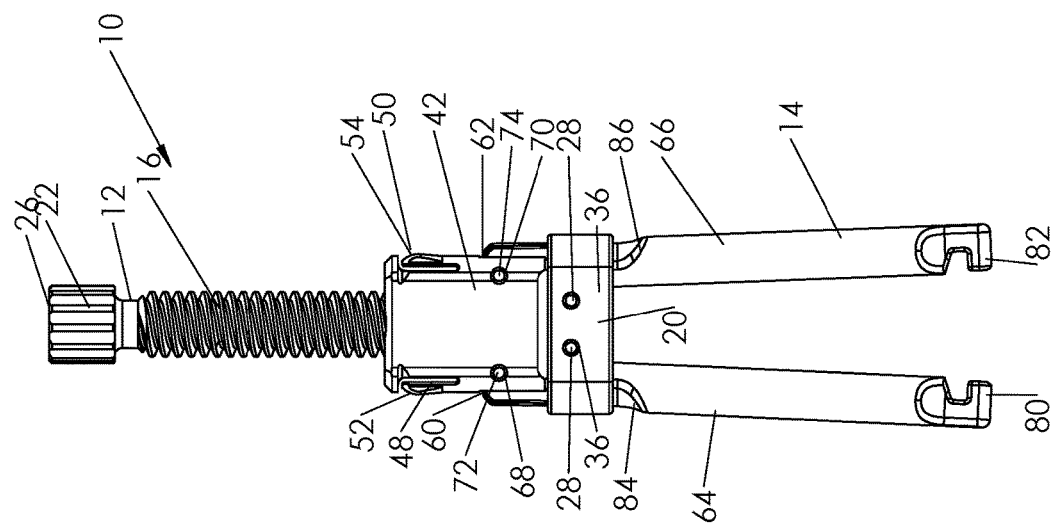

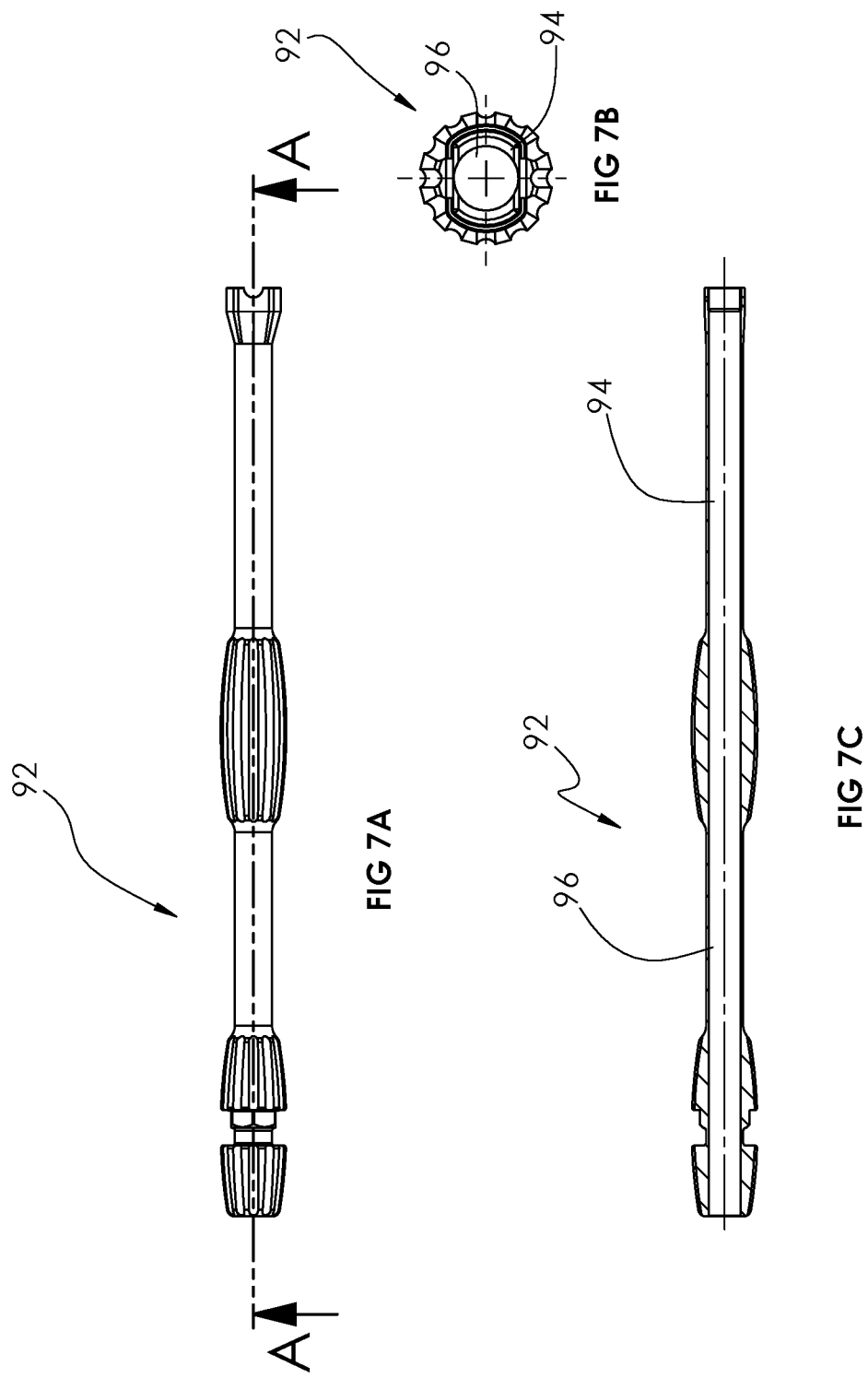

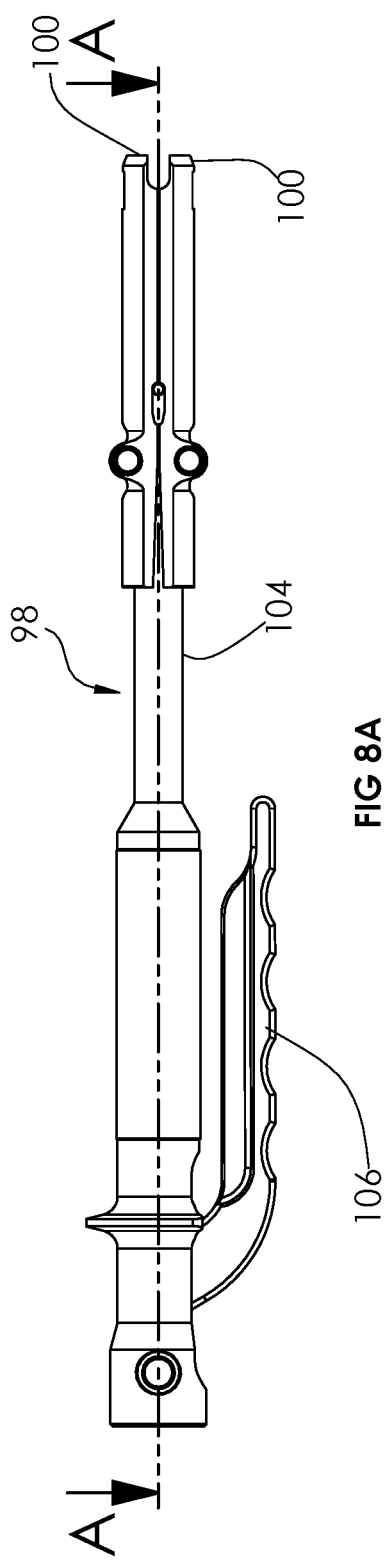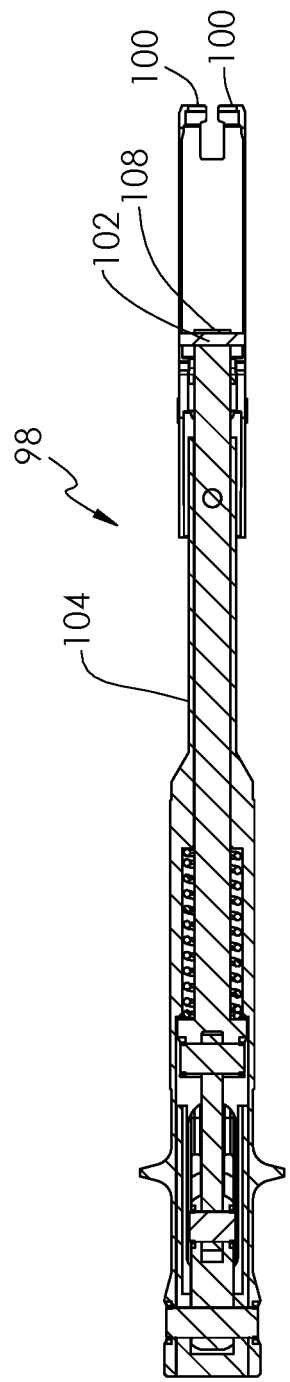
FIG 8A
FIG 8B

ROD REDUCTION DEVICE AND METHOD OF USE

CROSS-REFERENCE TO RELATED APPLICATIONS

This application is a continuation of U.S. patent application Ser. No. 15/496,768, filed on Apr. 25, 2017, which is a continuation of U.S. patent application Ser. No. 15/394,025, filed on Dec. 29, 2016, now U.S. Pat. No. 9,655,664, which is a divisional of U.S. patent application Ser. No. 14/609,868, filed on Jan. 30, 2015, now U.S. Pat. No. 9,532,816, which is a continuation of U.S. patent application Ser. No. 11/777,730, filed on Jul. 13, 2007, now U.S. Pat. No. 8,961,523, the entire contents of each of which are hereby incorporated by reference.

BACKGROUND OF THE INVENTION

Technical Field

The present invention relates to orthopedic surgery and in particular to devices for stabilizing and fixing the bones and joints of the body. Particularly, the present invention relates to a manually operated device capable of reducing a rod into position in a rod receiving notch in the head of a bone screw with a controlled, measured action.

Background Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions.

There are various disorders, diseases and types of injury, which the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to eliminate motion at the intervertebral disc or joint. To achieve this, natural or artificial bone, along with a spacing device, replaces part or all of the intervertebral disc to form a rigid column of bone, which is stabilized by mechanical hardware.

The mechanical hardware used to immobilize the spinal column typically involves a series of bone screws and metal rods or plates. When the spine surgery is performed posteriorly, it is common practice to place bone screws into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of a bone screw and then securing that connecting rod in place often can require that the surgeon use a number of instruments and expend a great deal of time and effort to accomplish the task. When bone screws in several adjacent vertebrae are to be securely connected by a spinal rod, the repeated process of inserting the rod into the heads of the bone screws and then securing the rod in place for each respective bone screw can be difficult, tiresome and time consuming. Further, the alignment of the rod as it connects to each of the sequential bone screws may require adjustment during the procedure and, therefore it is necessary that a device and method be provided by which the rod can be reduced into the head of each of the sequentially aligned bone screws and, as necessary, easily adjusted so as to facilitate the process for the surgeon with minimal effort and loss of time.

Conventional efforts to meet this need have fallen short in that no instrument has as yet been provided that effectively reduces in a controlled, measured way a connecting rod into position in the receiving slot of the head of a bone screw and holds that rod in position while other portions of the connecting rod are positioned and reduced into other bone screws allowing for position adjustment as necessary during the process.

For these reasons there remains a need for a device that is capable of securely grasping the head of a bone screw in a controlled, measured manner and reducing a posteriorly introduced rod into the head of that bone screw in such a way as to permit easy position adjustment as other portions of the rod are reduced into other bone screws.

SUMMARY OF THE DISCLOSURE

The present invention meets the above identified need by providing a novel device that grasps the head of a bone screw and reduces a rod into the rod receiving recess of the bone screw using a single manual control that can be activated in a controlled and measured manner.

Also provided is a novel rod reducing device that can reduce a rod into the rod receiving recess of a bone screw and adjustably hold that rod in the selected position during the process of reducing adjacent portions of the rod into other sequentially positioned bone screws.

Also provided is a novel rod reducing device having a screw jack mechanism capable of being manually operated in a controlled, measured manner to reduce a rod into position in the rod receiving recess of a bone screw.

Also provided is a novel rod reducing device including a screw jack mechanism moveably engaged with a grasping fork assembly, which includes two elongated, opposing grasping members, a controlling end of the screw jack mechanism being disposed proximal to the grasping fork assembly and a rod contacting distal portion of the screw jack mechanism being slidably engaged with the two grasping members of the grasping fork assembly.

Also provided is a novel rod reducing device including a screw jack mechanism and a moveably engaged grasping fork assembly, the screw jack mechanism having an elongated threaded portion, a portion of which is disposed between the two opposing grasping members of the fork assembly, that portion of the elongated threaded portion of the jack assembly terminating at its most distal end in connection with a rod contact surface.

Also provided is a novel rod reducing device including a screw jack mechanism moveably engaged with an elongated grasping fork assembly, the screw jack mechanism having an elongated threaded portion, the elongated threaded portion being connected at its most distal end to a rod contact member, which is positioned in sliding circumferential contact with each of the two opposing elongated grasping members and the most proximal end of the elongated threaded portion terminating in a controlling member which is disposed proximal to the grasping fork assembly of the device.

Also provided is a novel rod reducing device including a screw jack mechanism moveably engaged with an elongated grasping fork assembly, the grasping fork assembly having two elongated grasping members that each terminate in grasping elements that have a complimentary geometry to that of the bone screw head into which the rod is to be reduced so as to facilitates grasping contact.

Also provided is a method of using the novel rod reducing device to position a rod into the receiving recess of a bone screw head.

Also provided is a kit that can include at least one novel rod reducing device and at least one rod.

Also provided is a kit that can include at least one novel rod reducing device and at least one additional orthopedic device or instrument.

BRIEF DESCRIPTION OF THE DRAWINGS

The foregoing and other features of the disclosed device will become apparent to one skilled in the art to which the present invention relates upon consideration of the following description of exemplary embodiments with reference to the accompanying drawings, wherein:

FIGS. 3A-B respectively show a top view and cross sectional view A-A of the novel rod reducing device.

FIG. 5 shows a front view of the novel rod reducing device in a ready configuration.

FIGS. 7A-C respectively show a front view and a cross sectional view A-A of an alignment tube accessory for use in combination with the novel rod reducing device shown in FIGS. 1-5.

FIGS. 8A-B respectively show a front and cross-sectional view A-A of a partial locking device accessory for use in combination with the novel rod reducing device shown in FIGS. 1-5.

DETAILED DESCRIPTION OF PREFERRED EMBODIMENTS

Figure 1:
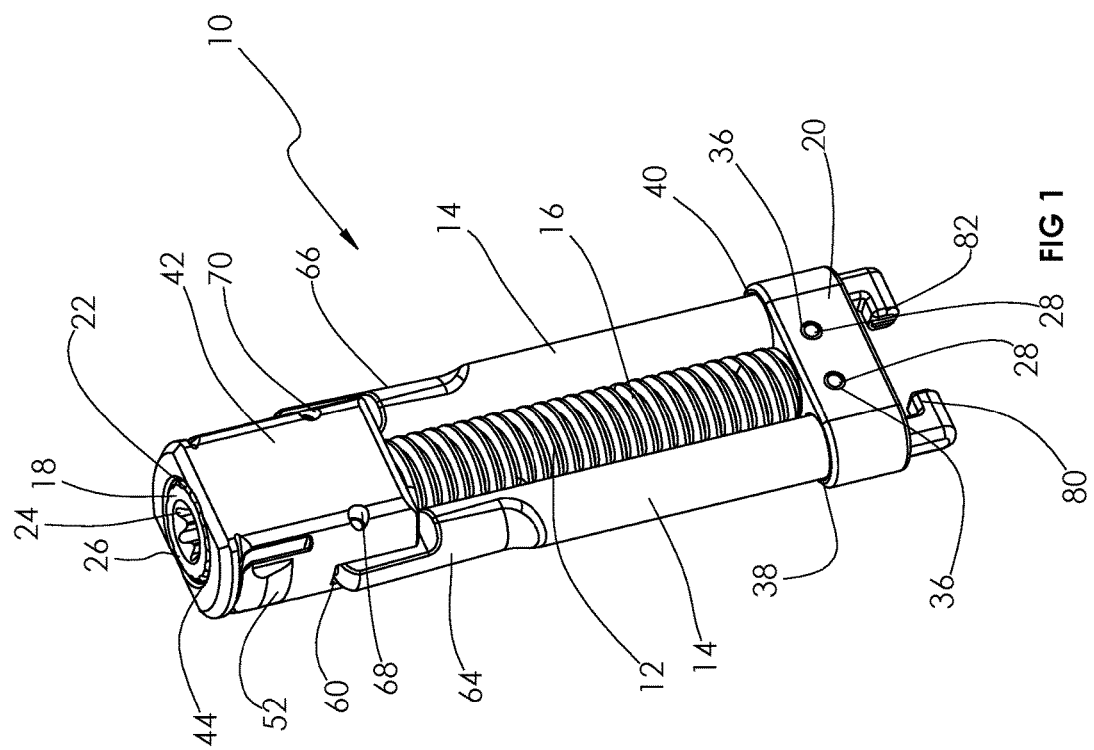
FIG. 1 shows an isometric view of the novel rod reducing device in an activated configuration; that is, with the screwjack mechanism fully inserted into a rod reduced configuration.

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

The device, as generally shown at 10 in FIGS. 1-6 is a rod reduction device capable of reducing a rod into position in a rod receiving notch in the head of a bone screw with a controlled, measured action. The device is an elongated rod reduction device 10 that includes a screw jack mechanism 12 moveably engaged with an elongated grasping fork assembly 14. The screwjack mechanism 12 includes an elongated threaded screw shaft 16 that terminates at its most proximal end with a controlling member 18 and terminates at its most distal end with a rod contact member 20.

Figure 6A:
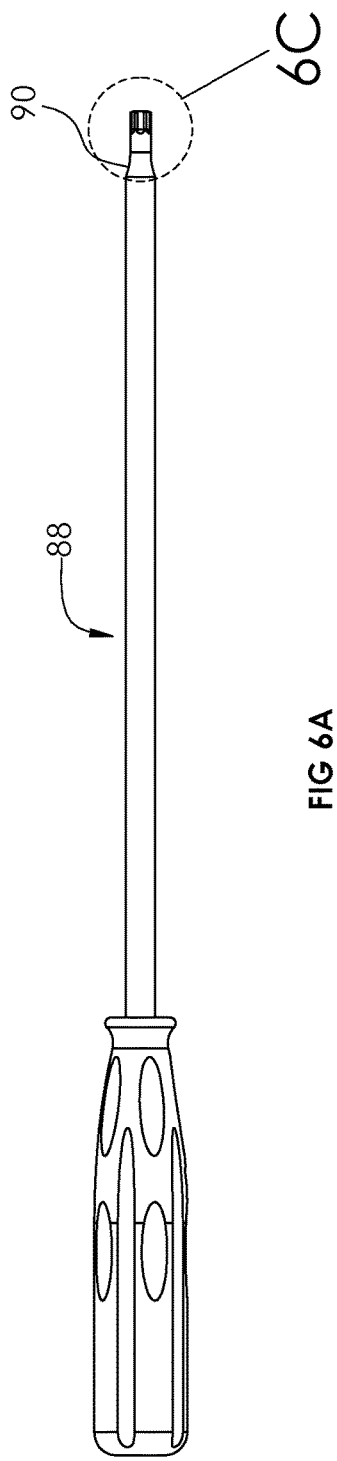
FIGS. 6A-C respectively show a front view, an enlarged distal end view (Scale 4:1), and an enlarged Detail "A" view (Scale 4:1) of a manually operated tool configured to engage with the engagement recess 24 of the novel rod reducing device shown in FIGS. 1-5.
Figure 6C:
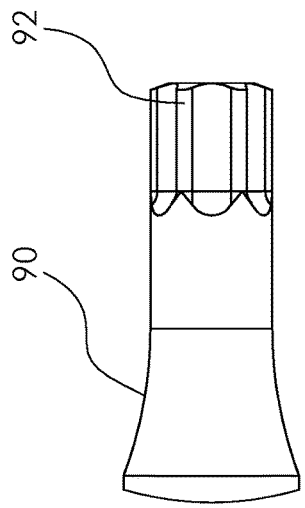
Figure 6B:
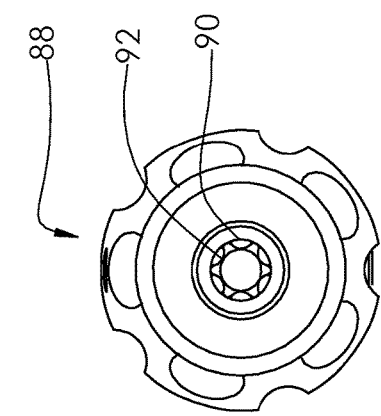

The controlling member 18, as shown in FIGS. 1, 3A, 4 and 5, includes circumferentially disposed gripping contacts 22, which facilitate the user's manual or instrumental grip on the controlling member during use. A tool engagement recess 24, as shown in FIGS. 1, 3A-B and 4, can be defined in the upper surface 26 of the controlling member 18. The tool engagement recess can be configured to complement the shape of a tightening or loosening tool that can be useful to facilitate rotational movement of the controlling member 18 of the elongated screw shaft 16. A non-limiting example of such a tool, generally shown at 88, that can be used to with the device is shown in FIGS. 6A-C. The exemplary tool 88 can be configured and operated in a similar manner to a screw driver; however, any tool known in the art that is capable of transmitting rotational tightening or loosening torque to the controlling member 18 of device 10 can be used. As shown in the enlarged detail of the distal end 90 of the tool 88, a controlling member engagement end 92 can be provided with a complementary configuration to that of the tool engagement recess 24 of the controlling member 18 of device 10. This complementary configuration of the engagement end 92 of the tool 88 and the engagement recess 24 of the device 10 can be of any shape that facilitates a positive engagement during the transmission of torque through the tool 88 to the device 10. Advantageously, the manual rotational movement of the controlling member 18 allows the user to activate the device 10 in a measured and controlled manner as compared to many conventional devices that are more abruptly activated. Any configuration of the tool engagement recess is within the scope of the invention so long as it facilitates engagement of the controlling member 18 with a tightening or loosening tool employed by a user of the device 10.

Figure 2:
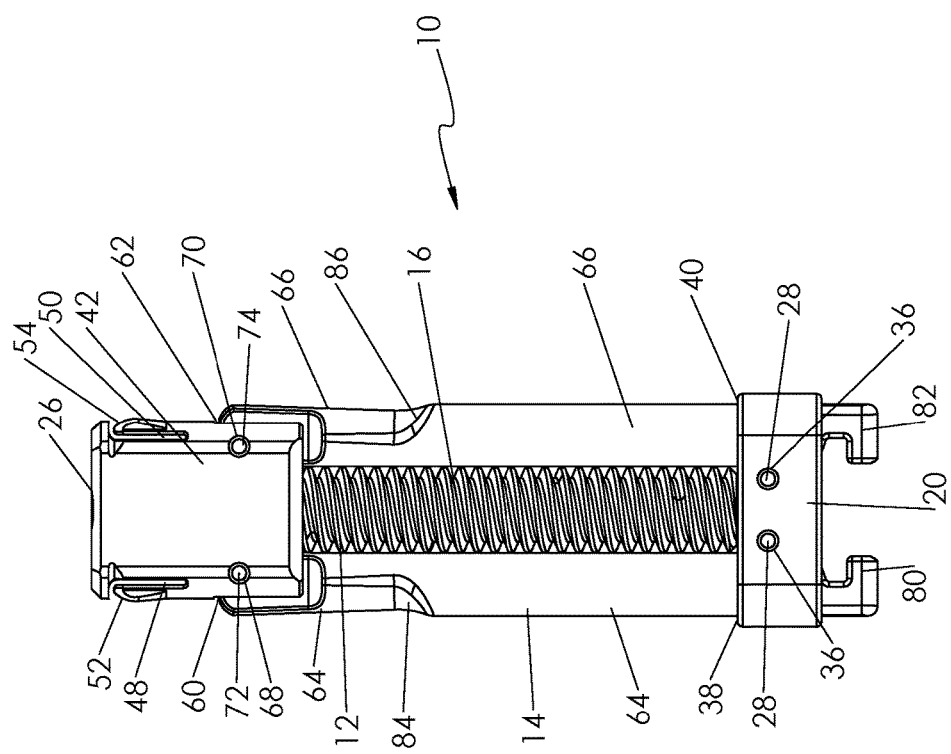
FIG. 2 shows a front view of the novel rod reducing device in an activated configuration.

As shown in FIGS. 1, 2, 3B, 4 and 5 the rod contact member 20 is connected to the distal end of the elongated threaded screw shaft 16 of the screw jack mechanism 12 by contact member retention pins 28. As shown in FIG. 2 and in the cross-sectional view of FIG. 3B the rod contact member retention pins 28 pass through retention pin holes 36 defined in the rod contact member 20 at a position that permits the retention pins 28 to also rest within a retention pin groove 30 that is circumferentially defined in the lower most portion 34 of the elongated threaded screw shaft 16. The lower most portion 34 of the threaded shaft 16 is not threaded but rather is configured to have a smooth surface that can facilitate free rotational movement of that portion of the shaft within an appropriately sized and configured contact member shaft well 32 defined in the contact member and best shown in the cross-sectional view of FIG. 3B. During assembly of the screw jack mechanism 12, the smooth lower most portion 34 of the elongated threaded screw shaft 16 is inserted into the contact member shaft well 32 and is then rotationally retained therein by the insertion of the contact member retention pins 28. The contact member shaft well 32 is sized and configured to receive the smooth surfaced lower most portion 34 of the distal end of the threaded shaft 16 and to allow free rotational movement of that lower most portion 34.

As shown in FIGS. 1, 2, 3B, 4 and 5, the rod contact member 20 defines at the first and second opposing ends of the contact member 20 a first and a second through passage 38, 40. The first and second through passage 38, 40 are sized and configured to facilitate the engagement of the elongated grasping fork assembly 14 with the screw jack mechanism 12 of the device 10.

Figure 4:
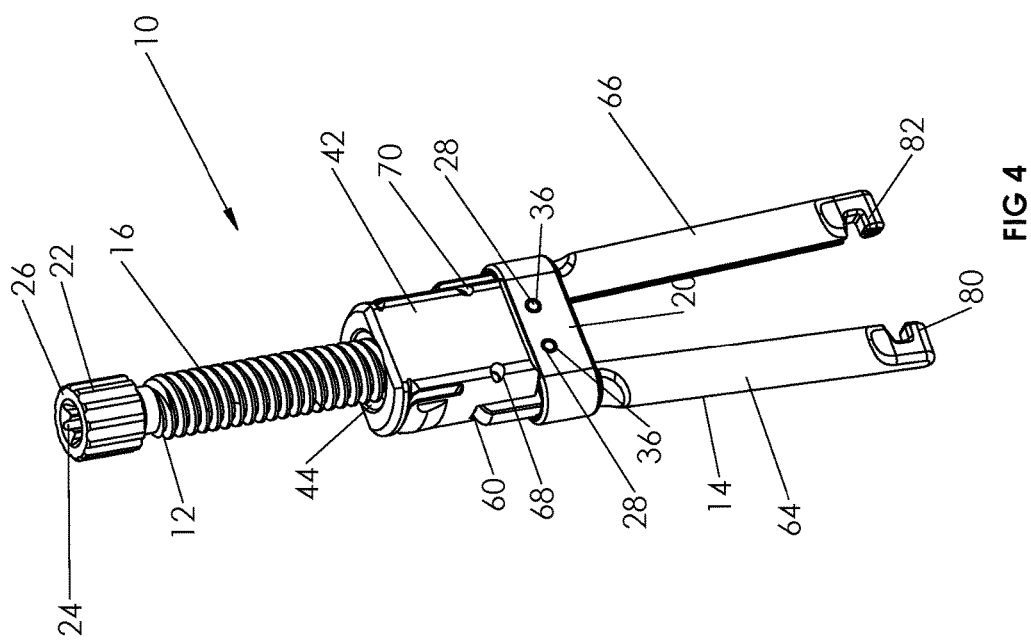
FIG. 4 shows an isometric view of the novel rod reducing device in a ready configuration; that is with the screw jack mechanism fully retracted and the two elongated grasping members in an open configuration.

The elongated grasping fork assembly 14 includes a fork assembly body 42. As shown in FIGS. 3B and 4 the fork assembly body 42 defines a body through passage 44 that is sized and complimentary configured to permit passage of the elongated threaded screw shaft 16 of the screw jack mechanism 12. The upper portion 46 of the body through passage 44 is provided without threads so as to allow the controlling member 18 to pass into that upper portion 46 of the passage; however, as shown in the cross-sectional view of FIG. 3B, the lower portion of the body through passage 44 is provided with complimentary threads to the threads of the elongated threaded screw shaft 16.

As best shown in FIGS. 2 and 3B, a first and second compression slot 48, 50 are defined on opposing sides of the fork assembly body 42. Outer most from the compression slots 48, 50 are associated first and second accessory connection tabs 52, 54, which, as best seen in FIG. 3B extend proximally from the inferior portions 56, 58 of the fork assembly body.

The first and second accessory connection tabs 52, 54 are provided to facilitate a positive engagement with other instruments or accessories that can be used in combination with the device 10, such as, for example the alignment tube, generally shown at 92 in FIG. 7-C. The exemplary embodiment of the alignment tube 92 is provided as a trocar-like device sized and configured to be circumferentially disposed around the device 10 and to be useful in the positioning of the device 10 in a patient. The accessory connection tabs 52, 54 extending outward from the fork assembly body 42 of device 10 can make sufficient contact with the inner wall 94 of the lumen 96 of the alignment tube 92 so as to facilitate movement of the device 10 into a proper position over the head of a bone screw into which a rod is to be placed. The alignment tube 92 can be provided with additional lumens or accessories to improve its usefulness in facilitating the positioning of device 10 over the bone screw during a surgical procedure.

In addition to facilitating the connection of accessories to the device 10, the connection tabs, 52, 54 when manually compressed inward can affect an outward bias of the inferior portions 56, 58 of the fork assembly body so as to slightly relieve pressure on the threaded portion of the body through passage 44 from the threadably engaged threaded screw shaft 16 of the screw jack mechanism 12. This additional advantage of the connection tabs 52, 54 can provide some relief of inward pressure during the manual rotation of the controlling member 18 and the threaded screw shaft 16 and conversely, when no pressure is manually applied to the accessory connection tabs 52, 54, the inward bias of the threaded portion of the body 44 serves to hold the threaded shaft 16 in its place and so provide a position securing effect that can be released at will by the user.

The fork assembly body 42 also defines opposing first and second pivot slots 60, 62 configured to pivotally receive first and second opposing elongated grasping members 64, 66 of the fork assembly 14. The fork assembly body 42, as shown in FIGS. 1, 2, 4 and 5 defines first and second body through holes 68, 70 sized to receive first and second body pins 72, 74, which serve as assembly pins for the fork assembly 14 and also serve as pivot pins to permit limited pivotal movement of the first and second elongated grasping members 64, 66 during operation of the device 10. As shown in FIG. 3B this limited pivotal motion is facilitated by pin 72, 74 insertion through appropriately sized grasping member pivot holes 76, 78, which are provided in each of the proximal ends of the elongated grasping members 64, 66.

The distal ends of each of the elongated grasping members 64, 66 of the grasping fork assembly 14 terminate in opposing first and second screw grasping elements 80, 82, which are sized and configured to complement corresponding grasping element receiving structures on the head of the bone screw into which the rod is to be reduced by the novel device 10. Any complementary configuration of grasping elements 80, 82 and receiving structure on a bone screw is within the concept of the invention. For illustration purposes, the present disclosure provides the non-limiting example of grasping elements 80, 82 as shown in the figures, which are complementary in configuration to the receiving notches of the bone screw heads shown in the commonly assigned U.S. patent application Ser. Nos. 11/493,624 and 11/493,625, the complete disclosures of which are fully incorporated herein by reference.

As shown in FIGS. 1, 2, 3B, 4 and 5 the upper portion of the first and second grasping members 64, 66 are provided with cam surfaces 84, 86 located distal to the respective grasping member pivot holes 76, 78. These cam surfaces 84, 86 are configured to interact with the interior wall of the respective first and second through passages 38, 40 of the rod contact member 20. In operation as controlling member 18 is activated so as to screw the elongated threaded screw shaft 16 into the fork assembly body 42, the rod contact member 20, which is attached to the distal end of the elongated threaded screw shaft 16, will be forced downward along the length of the opposing first and second grasping members 64, 66 of the grasping fork assembly 14. As the rod contact member 20 passes downward over the cam surfaces 84, 86 the interaction of the outwardly directed shape of the grasping members 64, 66 with the first and second through passages 38, 40 of the rod contact member 20 will serve to force the opposing grasping members 64, 66 inward toward one another to the end that the opposing first and second screw grasping elements 82, 84 will be forced inward to make grasping contact with a complimentary configured bone screw head. As the controlling member 18 is manually directed further inward, the rod contact member will be brought to bear against a rod positioned over the screw, which is firmly grasped by the grasping elements 80, 82 of the device. Thus, by the simple manual activation of the device 10, as shown in FIGS. 1, 2 and 3B, a rod can be forced downward into a receiving recess of a bone screw head that is securely held by the grasping elements 80, 82 of the device 10. A reversal of the direction of motion of the controlling member 18 so as to withdraw the screw jack mechanism outwardly from the activated position of the device as shown in FIGS. 1, 2 and 3B will result in the interaction of the cam surfaces 84, 86 releasing the inward pressure of the opposing grasping members 64, 66 and thus releasing the hold of the grasping elements 80, 82 on the bone screw head.

It is within the concept of the invention that the configuration of the different elements of the device can be varied or altered from the non-limiting examples described herein without departing from the concept of the invention. For example, the grasping members 64, 66, which are illustrated in the figures in a preferred round cross-sectional configuration, can be provided as flat, square, or any other shape as might be determined advantageous or desirable. Further, the provision of additional elements such as guiding bars or associated guide grooves on the elements of the invention that during operation are in a sliding operation relative to each other would not be a departure from the invention disclosed herein and defined by the claims presented below. For example, complimentary guiding grooves, or slots could be provided in the elongated grasping members 64, 66, which slide within the through passages, 38, 40 of the rod contact member 20.

The inventors have contemplated that a series of the novel devices 10 disclosed herein can be employed to effect the reduction of a rod into the receiving recess of multiple sequentially aligned bone screws.

The device 10 can be manufactured as integral components by methods known in the art, to include, for example, molding, casting, forming or extruding, and machining processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose.

In addition to the alignment tube 92, discussed above, another orthopedic instrument that can be used in combination with the rod reduction device 10 is a partial locking device, generally shown at 98 in FIGS. 8A-B. After the rod reduction device 10 of the present invention has been used to reduce a rod into the rod receiving notch in the head of a bone screw, the partial locker device 98 can be used to engage the bone screw and lock the rod into place. The partial locking device 98 can be provided with opposing screw grasping elements 100, which are configured to grasp an outer housing of a bone screw having an inner and outer housing taper lock mechanism. In operation, an inner locking shaft 102 that is slidably disposed within the housing 104 can be moved by a pivotally mounted activation handle 106 such that the contact end 108 of the shaft 102 is brought into operational contact with the top of rod reduction device 10 while the grasping elements 100 pull the outer housing of the screw upward over the screw inner housing into a partial or fully locked position. The mechanism and operational characteristics of the exemplary partial locking device 98 is similar to the screw locking device disclosed in U.S. patent application Ser. No. 11/493,624, which is fully incorporated herein by reference. While partial locking device 98 is generally disclosed herein as a non-limiting example of a locking device that can be employed in combination with the rod reduction device 10 of the present invention, it is within the inventor's concept that any locking device configured to facilitate locking of the rod within the head of a bone screw can be employed in combination with device 10.

It is also within the concept of the present invention to provide a kit, which includes the novel rod reduction device disclosed herein. Additionally, a kit can include a rod or rods adaptable for use with the disclosed device. Further, bone screws which are formed with a complimentary configuration for use with the disclosed rod reduction device can be included. A non-limiting example of such a screw is the taper lock screw disclosed and claimed in commonly assigned U.S. patent application Ser. Nos. 11/493,624 and 11/493,625, which are fully incorporated herein by reference. Additional tools and surgical instruments such as the alignment tube 92, the partial locking device 98, and the tool 88 can also be included with the device 10 in a kit. Other orthopedic devices such as cross-connectors, hooks, or links can also be included in the kit. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A rod reducing device comprising:
   a fork assembly body defining a longitudinal axis and having a passage extending therethrough along the longitudinal axis thereof, the passage including internal threads;
   a first arm coupled to and extending from a first side of the fork assembly body;
   a second arm coupled to and extending from a second side of the fork assembly body, the second side different from the first side; and
   an elongated threaded screw shaft having external threads thereon, each of the first and second arms transitionable relative to the elongated threaded screw shaft between an approximated arrangement and a spaced apart arrangement with the elongated threaded screw shaft rotatably coupled with the internal threads of the passage, wherein a rod contact member is disposed at a distal portion of the elongated threaded screw shaft, the distal portion of the elongated threaded screw shaft and the rod contact member movable between the first and second arms in response to engagement of the threads of the elongated threaded screw shaft with the internal threads of the passage.

2. The rod reducing device of claim 1, wherein the first and second arms are transitionable between a non-parallel arrangement and a parallel arrangement, the parallel arrangement of the first and second arms grasping a portion of a bone anchor between the first and second arms.

3. The rod reducing device of claim 2, wherein the parallel arrangement of the first and second arms defines a first distance between distal portions of the first and second arms, and wherein the non-parallel arrangement of the first and second arms defines a second distance between the distal portions of the first and second arms which is greater than the first distance.

4. The rod reducing device of claim 1, wherein a distal portion of the first arm includes a first protrusion and a distal portion of the second arm includes a second protrusion, the first and second protrusions extending towards each other to contact complementary portions of a bone anchor therebetween.

5. The rod reducing device of claim 1, wherein rotation of the elongated threaded screw shaft in threaded engagement with the internal threads of the passage causes the rod contact member to move distally along the longitudinal axis of the fork assembly body to contact a rod and urge the rod disposed between the first and second arms towards distal ends of the first and second arms.

6. The rod reducing device of claim 5, wherein rotation of the elongated threaded screw shaft in threaded engagement with the internal threads of the passage rotates the elongated threaded screw shaft relative to the rod contact member.

7. The rod reducing device of claim 1, wherein rotation of the elongated threaded screw shaft in threaded engagement with the internal threads of the passage causes the rod contact member to move distally towards distal ends of the first and second arms.

8. The rod reducing device of claim 1, wherein the rod contact member defines through passages for movement along the first and second arms.

9. The rod reducing device of claim 8, further including camming surfaces located on the first and second arms.

10. The rod reducing device of claim 1, wherein distal movement of the rod contact member urges the rod contact member into contact with a rod disposed between the first and second arms to urge the rod towards distal ends of the first and second arms.

11. The rod reducing device of claim 1, wherein the distal portion of the elongated threaded screw shaft and the rod contact member move in a plane defined by the first and second arms to contact the rod.

12. The rod reducing device of claim 1, wherein the first and second arms extend distally from the fork assembly body.

13. The rod reducing device of claim 1, wherein the rod contact member is connected to the distal portion of the elongated threaded screw shaft and the elongated threaded screw shaft being rotatable relative to the rod contact member.

14. The rod reducing device of claim 1, wherein a longitudinal axis of the elongated threaded screw shaft is coincident with the longitudinal axis of the fork assembly body.

15. The rod reducing device of claim 1, wherein the distal portion of the elongated threaded screw shaft is coincident with the longitudinal axis of the fork assembly body.

16. The rod reducing device of claim 1, where the distal portion of the elongated threaded screw shaft and the rod contact member move along the longitudinal axis of the elongated threaded screw shaft between the first and second arms to urge the rod towards distal ends of the first and second arms.

17. The rod reducing device of claim 1, wherein the fork assembly body is unitary.

18. The rod reducing device of claim 1, wherein rotation of the elongated threaded screw shaft in threaded engagement with the internal threads of the passage moves the distal portion of the elongated threaded screw shaft such that at least some of the threads of the elongated threaded screw shaft are visible between the first and second arms.

19. The rod reducing device of claim 1, wherein the approximated arrangement of the first and second arms grasps a portion of a bone anchor positioned between the first and second arms.

20. A rod reducing device comprising:
a fork assembly body defining a longitudinal axis and having a passage extending therethrough along the longitudinal axis thereof, the passage including internal threads;
a first arm extending from a first side of the fork assembly body;
a second arm extending from a second side of the fork assembly body, the second side different from the first side, the first and second arms transitionable between a non-parallel arrangement and a parallel arrangement, the parallel arrangement contacting a portion of a bone anchor; and
an elongated threaded screw shaft having external threads thereon that is rotatably coupled with the internal threads of the passage, wherein a rod contact member is positioned at a distal portion of the elongated threaded screw shaft, the distal portion of the elongated threaded screw shaft and the rod contact member movable between the first and second arms in response to engagement of the threads of the elongated threaded screw shaft with the internal threads of the passage, wherein the first and second arms are transitionable between the non-parallel arrangement and the parallel arrangement with the elongated threaded screw shaft rotatably coupled with the internal threads of the passage.

21. A rod reducing device comprising:
a fork assembly body defining a longitudinal axis and having a passage extending therethrough along the longitudinal axis thereof, the passage including internal threads;
a first arm coupled to a first side of the fork assembly body;
a second arm coupled a second side of the fork assembly body, the second side different from the first side;
an elongated threaded screw shaft having external threads thereon that is rotatably coupled with the internal threads of the passage, wherein a rod contact member is located at a distal portion of the elongated threaded screw shaft, the distal portion of the elongated threaded screw shaft and the rod contact member movable between the first and second arms in response to engagement of the threads of the elongated threaded screw shaft with the internal threads of the passage;
a first screw grasping element disposed on the first arm; and
a second screw grasping element disposed on the second arm, each of the first and second screw grasping elements repositionable relative to the longitudinal axis of the fork assembly body with the elongated threaded screw shaft rotatably coupled with the internal threads of the passage, the first and second screw grasping elements assuming an approximated configuration defining a first gap and an open configuration defining a second gap greater than the first gap, the first gap for grasping a portion of a bone anchor between the first and second screw grasping members.

22. The rod reducing device of claim 21, wherein the first and second arms define a parallel arrangement in the approximated configuration and a non-parallel arrangement in the open configuration, the parallel arrangement of the first and second arms grasping a portion of the bone anchor between the first and second arms.

23. The rod reducing device of claim 22, wherein the parallel arrangement of the first and second arms defines a first distance between distal portions of the first and second arms, and the non-parallel arrangement of the first and second arms defines a second distance between the distal portions of the first and second arms which is greater than the first distance.

24. The rod reducing device of claim 21, wherein rotation of the elongated threaded screw shaft in threaded engagement with the internal threads of the passage causes the rod contact member to move distally along the longitudinal axis of the fork assembly body to contact a rod and urge the rod disposed between the first and second arms towards distal ends of the first and second arms.

25. The rod reducing device of claim 24, wherein rotation of the elongated threaded screw shaft in threaded engagement with the internal threads of the passage rotates the elongated threaded screw shaft relative to the rod contact member.

26. The rod reducing device of claim 21, wherein the rod contact member is connected to the distal portion of the elongated threaded screw shaft and the elongated threaded screw shaft rotatable relative to the rod contact member.

27. The rod reducing device of claim 21, wherein rotation of the elongated threaded screw shaft in threaded engagement with the internal threads of the passage moves the distal portion of the elongated threaded screw shaft such that at least some of the threads of the elongated threaded screw shaft are visible between the first and second arms.

* * * * *